United States Patent [19]

Remy

[11] Patent Number: 4,639,457
[45] Date of Patent: Jan. 27, 1987

[54] BENZOCYCLOHEPTAPYRIDONE COMPOUNDS FOR TREATING CONGESTIVE HEART FAILURE

[75] Inventor: David C. Remy, North Wales, Pa.

[73] Assignee: Merck & Co., Inc., Rahway, N.J.

[21] Appl. No.: 766,472

[22] Filed: Aug. 19, 1985

[51] Int. Cl.$^4$ .................... A61K 31/44; C07D 221/16
[52] U.S. Cl. ...................................... 514/290; 546/93
[58] Field of Search .......................... 546/93; 514/290

[56] References Cited

U.S. PATENT DOCUMENTS 3,357,986 12/1967 Villani .................................. 546/93
4,034,095 7/1977 Bastian .............................. 546/93 X
4,511,569 4/1985 Smith et al. ........................ 514/290

FOREIGN PATENT DOCUMENTS 102046 3/1984 European Pat. Off. ............. 546/93

*Primary Examiner*—Richard A. Schwartz
*Attorney, Agent, or Firm*—Alice O. Robertson; Michael C. Sudol

[57] ABSTRACT

Novel benzocycloheptapyridone compounds are disclosed. The compounds exhibit inotropic potencies and are adaptable to being utilized as cardiotonic agents in the chemotherapeutic treatment of cardiovascular diseases.

9 Claims, No Drawings

BENZOCYCLOHEPTAPYRIDONE COMPOUNDS FOR TREATING CONGESTIVE HEART FAILURE

DESCRIPTION OF THE INVENTION

The present invention is directed to novel benzocycloheptapyridone compounds represented by the formula:

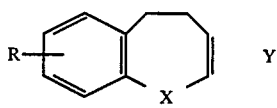 (I)

In this and succeeding formulas, the ------ bond designation indicates that the bond may be a saturated single bond or an unsaturated double bond; X is —C=O or —CHOH; Y is —NHCOCH=CH—; and R is hydrogen, lower alkoxy, cyano, trifluoromethylthio, lower alkylthio or halogen. The chain represented by Y may be attached at either position of the cycloheptane ring. Thus, either the amido nitrogen or the ethylenic carbon may be attached to the carbon adjacent to X. When the amido nitrogen is attached to the carbon adjacent to X, the compounds may be represented by the following formula (IA):

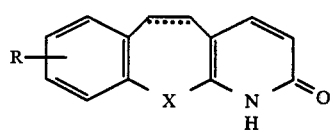 (IA)

When the ethylenic carbon is attached to the carbon adjacent to X, the compounds may be represented by the following formula (IB):

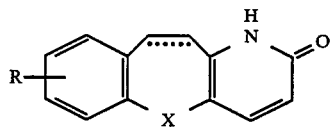 (IB)

The expressions "lower alkoxy" and "lower alkylthio" refer to radicals having from 1 to 6 carbon atoms, inclusive.

By "halogen" is meant fluorine, chlorine, bromine or iodine.

The compounds of the present invention are generally white crystalline solids. Some of the products have been found to crystallize as solvates.

The compounds have shown inotropic properties which would render them useful as cardiotonic agents in the chemotherapeutic treatment of cardiovascular diseases such as congestive heart failure. Compositions containing these compounds and methods for using these compounds as cardiotonic agents constitute an aspect of the present invention.

The preparation of the compounds of the present invention entails the formation of an N-oxide in the pyridine ring and the subsequent rearrangement to a pyridone compound, a compound of the present invention in which X is C=O. When compounds are desired in which X is CHOH, the pyridone compound is reduced as subsequently described.

The compounds of the present invention in which X is C=O, represented by Formula IA or IB, may be prepared by causing a compound of Formula A or A' to react with a peracid to form first an N-oxide intermediate of Formula B or B' and thereafter reacting the N-oxide with p-toluenesulfonyl (hereinafter tosyl) chloride and potassium carbonate to obtain the desired compounds represented by Formula IA or IB. If desired, the compounds of Formula IA or IB may be reduced to form compounds in which X is CHOH, represented by Formulas IC and ID. The reactions may be seen in the following flow diagrams:

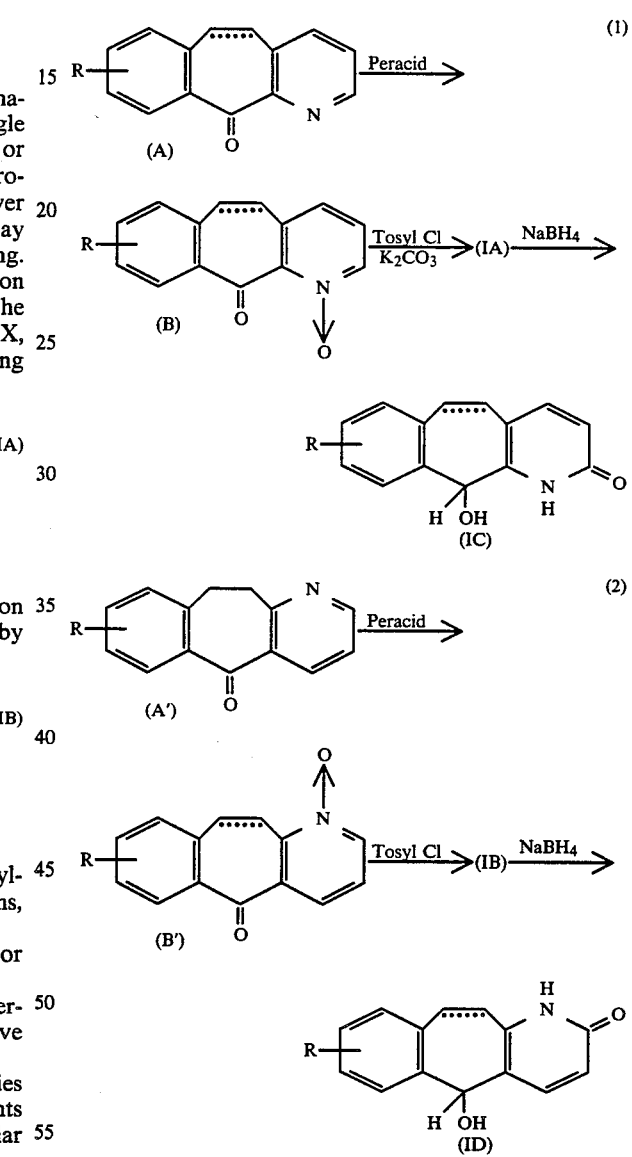

For the preparation of the N-oxide, the appropriate oxobenzopyridine compound of Formula A or A' (hereinafter "pyridine compound") is oxidized with a peracid. A substantially equimolar amount of the peracid or a slight molar excess is employed. The reaction is generally carried out at ambient temperature for time sufficient to complete the reaction. Usually from about 24 to about 48 hours is employed.

Suitable per acids include m-chloroperbenzoic acid, perbenzoic acid, peracetic acid, perchloric acid, and pertrifluoroacetic acid.

The reaction is carried out in an inert solvent. Suitable solvents include chloroform, carbon tetrachloride, methylene chloride, ethylene dichloride, ethylene dibromide and the like.

In carrying out the reaction, a solution of the peracid in an inert solvent is added dropwise to a solution of the pyridine compound and the resulting solution stirred at ambient temperature for about 8 to 48 hours to obtain the N-oxide in the reaction mixture. The N-oxide is recovered from the reaction mixture by washing with aqueous alkali and water, drying, and vaporizing the solvent from the dried solution to obtain a residue.

The pyridone compound (IA or IB) may be obtained from the N-oxide (B or B') by reacting the N-oxide intermediate with tosyl chloride in an inert solvent and in intimate contact with a potassium carbonate solution. The tosyl chloride is employed in substantially equimolar amount or a slight excess. Suitable solvents include chloroform, carbon tetrachloride, ethylene dichloride, ethylene dibromide, methylene chloride and the like. The reaction is carried out for time sufficient to complete the formation of a compound represented by Formula IA or IB forms in the reaction mixture, generally a period of from about 1 to 6 days.

In carrying out the reaction, the N-oxide compound and tosyl chloride are placed in a solvent. To it then is added an aqueous potassium carbonate solution and the resulting mixture stirred vigorously whereupon a reaction takes place with the formation and separation as solid of the pyridone compound. The solid is recovered by filtration and washed, generally with aqueous alkali, water and an alcohol, and then dried to obtain the desired pyridone compound of Formula IA or IB.

When the product desired is a hydroxy compound of Formula IC or ID, the product of Formula IA or IB is employed as an intermediate and is reduced, employing a reagent which will selectively or preferentially reduce the carbonyl group on the cycloheptane ring without affecting the pyridone or lactam. Suitable reducing agents include sodium borohydride and lithium borohydride. Sodium borohydride is the preferred agent. Excess of the reducing agent is employed. About 2 to 3 molar excess of the reagent is suitable. The reduction is carried out in solution. Suitable solvents include methanol, ethanol, isopropanol and like alkanols.

In carrying out the reaction, an aqueous solution of sodium borohydride is added dropwise to a refluxing suspension of the pyridone compound in an alkanol preferably methanol. After completion of the addition, the heating under reflux of the mixture is continued until substantial completion of the reaction with the formation of the heptanol compound as determined by thin layer chromatographic (TLC) analysis. The product hydroxy compound of Formula IC or ID may be recovered from the reaction mixture employing conventional procedures, e.g. vaporizing the solvent and then washing, filtering and drying the residue.

The usefulness of the compounds of the present invention as cardiotonic agents may be demonstrated by testing for the positive inotropic activity on cardiac muscle. The property may be observed by measuring the inotropic potencies of the test compounds. The inotropic potency may be measured in a test in which papillary muscle from the right ventricle of cat heart are suspended in an aerated physiological solution in a tissue bath instrumented for recording isometric tension. A resting tension of 0.4 to 1 gram is applied to each muscle and the tissues are stimulated at a frequency of 1.0 Hz. To assess potential inotropic responsiveness, the maximal contractile force to paired pulse stimulation (70–140 msec between pulses) is determined. The tissues then are washed and re-equilibrated. The test compound is placed into the tissue bath and the maximal contractile force obtained at each concentration of the drug. From these results, inotropic potencies may be calculated. Potency is expressed as the effective concentration required to increase isometric tension of the cat papillary muscle by 200 mg, ($ED_{200}$ mg) When representative compounds of the present invention were employed in the test, the following results were obtained:

| Compound | $ED_{200}$ mg. Concentration |
|---|---|
| 5-Oxo-benzo[4,5]cyclohepta[1,2-b]-pyrid-2(1H)one | $5.26 \times 10^{-6}$ M |
| 9-Bromo-11-oxo-benzo[5,6]cyclohepta[1,2-b]pyrid-2(1H)one | $1.27 \times 10^{-5}$ M |
| 11-Oxo-benzo[5,6]cyclohepta[1,2-b]-pyrid-2(1H)one | $1.49 \times 10^{-5}$ M |

For use in the chemotherapeutic treatment of cardiovascular diseases, an effective amount of the compounds of the present invention may be administered orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration. The dosage level for the compounds may be varied from about 0.03 milligram to about 10 milligrams per kilogram of body weight per day. Daily doses in the range of 1 to 10 mg/kg are preferred. These doses are suitable for any of the methods of administration described herein.

To prepare the pharmaceutical compositions of this invention, the compounds of the present invention are intimately admixed with a pharmaceutical carrier according to conventional pharmaceutical compounding techniques, which carrier may take a wide variety of forms depending on the form of preparation desired for administration, e.g., oral or parenteral.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques.

For parenterals, the carrier will usually comprise sterile water, although other ingredients may be included, for purposes such as, for example, for aiding solubility or for preservation. Injectable suspensions also may be prepared, in which case appropriate liquid carriers, suspending agents and the like may be employed.

The pharmaceutical compositions herein will contain, per dosage unit, e.g., tablet, capsule, powder, injection, teaspoonful and the like, from about 10 to about 500 mg of the active ingredient, preferably, from about 10 to about 250 mg.

The following examples illustrate the invention but are not to be construed as limiting:

EXAMPLE I

5-Oxo-benzo[4,5]cyclohepta[1,2-b]pyrid-2(1H)one and its 0.25 methanol solvate

To a solution of 2.07 grams (0.01 mole) of benzo[4,5-]cyclohepta[1,2-b]pyridin-5-one in 25 milliliters of chloroform was added dropwise, a solution of 2.0 grams (0.01 mole) of m-chloroperbenzoic acid in 30 milliliters of chloroform and the resulting solution stirred for 7 hours at room temperature. At this time an additional 0.5 gram of m-chloroperbenzoic acid was added and the mixture stirred overnight at room temperature. The resulting reaction mixture was washed successively with two 100 milliliter portions of 10 percent aqueous sodium hydroxide and two 100 milliliter portions of water and then dried over magnesium sulfate. The dried solution was filtered to remove the drying agent and the chloroform was vaporized to obtain 2.23 grams of a benzo[4,5]cyclohepta[1,2-b]pyridin-5-one N-oxide intermediate.

To a solution of 2.23 grams (0.01 mole) of 5-oxo-benzo[4,5]cyclohepta[1,2-b]pyridine N-oxide intermediate and 2.29 grams (0.012 mole) of tosyl chloride in 100 milliliters of chloroform was added a solution of 1.76 grams of potassium carbonate in 25 milliliters of water and the resulting mixture stirred vigorously for 4 days at room temperature. During this period the desired 5-oxo-benzo[4,5]cyclohepta[1,2-b]pyrid-2(1H)one product formed in the reaction mixture as a solid. The solid was recovered by filtration, was washed successively with 10 percent sodium hydroxide solution, water and hot methanol, and was dried. The dried product was a TLC homogeneous 5-oxo-benzo-[4,5]cyclohepta[1,2-b]pyrid-2(1H)one.0.25 methanol solvate, m.p. 320° C. The elemental analyses were as follows:

Calc'd for $C_{14}H_9NO_2.0.25\ CH_3OH$:
C, 74.14; H, 4.33; N, 6.09.
Found: C, 74.28; H, 4.05; N, 5.71.

EXAMPLE II

11-Oxo-benzo[5,6]cyclohepta[1,2-b]pyrid-2(1H)one

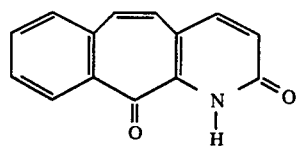

To a solution of 1.04 grams (0.005 mole) of benzo[5,6-]cyclohepta[1,2-b]pyridin-11-one in 20 milliliters of chloroform was added 1.19 grams (0.0055 mole) of m-chloroperbenzoic acid and the resulting solution stirred at room temperature for 24 hours. At this time an additional 0.6 gram of m-chloroperbenzoic acid was added and the mixture stirred for 5 hours; thereafter, another 0.3 gram of m-chloroperbenzoic acid was added and the mixture stirred overnight. The resulting reaction mixture was then washed twice with 10 percent aqueous sodium hydroxide, twice with water and the washed solution dried over magnesium sulfate. The mixture was filtered to remove drying agent and the solvent removed under reduced pressure to obtain 0.75 gram of benzo[5,6]cyclohepta[1,2-b]pyridin-11-one N-oxide intermediate as residue.

To a solution of 0.75 gram (0.0034 mole) of the N-oxide thus obtained and 0.77 gram (0.0043 mole) of tosyl chloride in 37.5 milliliters of chloroform was added a solution of 0.58 gram (0.0042.mole) of potassium carbonate in 5.8 milliliters of water and the resulting mixture was stirred vigorously at room temperature for about 60 hours. At the end of this time the reaction mixture was washed with 10 percent aqueous sodium hydroxide whereupon a solid precipitated in the chloroform phase. The solid was recovered by filtration and recrystallized from isopropyl alcohol/methanol to obtain purified 1-oxo-benzo[5,6]cyclohepta[1,2-b]pyrid-2(1H)one product, m.p. 195°-196° C. The elemental analyses were as follows:

Calc'd for $C_{14}H_9NO$:
C, 75.33; H, 4.06; N, 6.28.
Found: C, 75.63; H, 4.09; N, 6.06.

EXAMPLE III

9-Bromo-11-oxo-benzo[5,6]cyclohepta[1,2-b]pyrid-2(1H)one

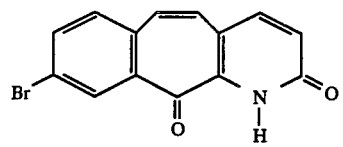

To a solution of 2.15 grams (0.0075 mole) of 9-bromo-11-oxo-benzo[5,6]cyclohepta-[1,2-b]pyridine in 40 milliliters of chloroform was added 1.78 grams (0.0082 mole) of m-chloroperbenzoic acid and the resulting solution was stirred at room temperature for about 24 hours. At this time, an additional 0.9 gram of m-chloroperbenzoic acid oxidant was added and the stirring continued for 5 hours, after which time, yet another 0.45 gram of the oxidant was added and the stirring continued overnight at room temperature. The resulting mixture was washed twice with 10 percent aqueous sodium hydroxide and twice with water and dried over magnesium sulfate. The drying agent was removed by filtration and the filtrate concentrated at reduced pressure to obtain a residue. The latter was triturated with acetonitrile to obtain 1.37 grams of 9-bromo-11-oxo-benzo[5,6]cyclohepta[1,2-b]pyridine N-oxide intermediate.

1.37 grams of the intermediate thus obtained and 1.04 grams (0.0054 mole) of tosyl chloride were dissolved in 70 milliliters of chloroform and to the resulting solution was added a solution of 0.78 gram (0.0057 mole) of potassium carbonate in 7.8 milliliters of water and the mixture stirred vigorously at room temperature for about 60 hours. At the end of this time, the reaction mixture was washed with 10 percent sodium hydroxide solution whereupon a solid precipitated. The latter was recovered by filtration, was washed with water and recrystallized from methanol to obtain the desired 9-bromo-11-oxo-benzo[5,6]cyclohepta[1,2-b]pyrid-2(1H)one product, m.p. 268°-269° C. The product had elemental analyses as follows:

Calc'd for C$_{14}$H$_8$BrNO$_2$:
C, 55.65; H, 2.67; N, 4.64.
Found: C, 55.71; H, 2.65; N, 4.42.

EXAMPLE IV

9-Cyano-11-oxo-5,6-dihydrobenzo[5,6]cyclohepta[1,2-b]pyrid-2(1H)one

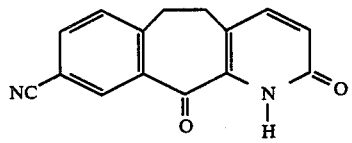

In a manner similar to that described in Example II, 1.19 grams (0.0055 mole) of m-chloroperbenzoic acid is added to a solution of 1.29 grams (0.005 mole) of 9-cyano-5,6-dihydrobenzo[5,6]cyclohepta[1,2-b]pyridin-11-one in 20 milliliters of chloroform and the resulting mixture stirred at ambient temperature for several days with an addition of an about 0.5 gram portion of m-chloroperbenzoic acid after the first 24 hours. At the end of this period the mixture is washed, dried and evaporated to obtain a 9-cyano-5,6-dihydrobenzo[5,6-]cyclohepta[1,2-b]-pyridin-11-one N-oxide intermediate as residue.

To a solution of 0.85 gram (0.0034 mole) of the N-oxide thus obtained and 0.77 gram (0.0043 mole) of tosyl chloride in 37.5 milliliters of chloroform was added a solution of 0.58 gram (0.0042 mole) of potassium carbonate in 5.8 milliliters of water and the resulting mixture was stirred vigorously at room temperature for two days and the reaction mixture washed with alkali to obtain an 11-oxo-5,6-dihydrobenzo[5,6]-cyclohepta[1,2-b]pyrid-2(1H)one product which is recovered and purified by conventional procedures.

EXAMPLE V

5-Oxo-7-trifluoromethylthio-10,11-dihydrobenzo[4,5-]cyclohepta[1,2-b]pyrid-2(1H)one

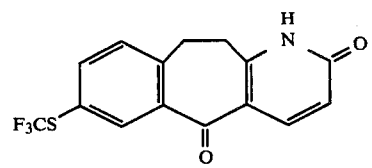

In a manner similar to that described in Example I, a solution of 2 grams (0.01 mole) of m-chloroperbenzoic acid in 30 milliliters of chloroform is added dropwise to a solution of 3.09 grams (0.01 mole) of 7-trifluoromethylthio-10,11-dihydrobenzo[4,5]cyclohepta[1,2-b]pyridin-5-one in 25 milliliters of chloroform and the resulting solution is stirred overnight at ambient temperature to obtain a 7-trifluoromethylthiodihydrobenzo[4,5]cyclohepta-1,2-b]pyridin-5-one N-oxide intermediate in the reaction mixture which may be recovered by conventional procedures.

To a solution of 3.25 grams (0.01 mole) of the N-oxide intermediate thus prepared and 2.29 grams (0.012 mole) of tosyl chloride in 100 milliliters of chloroform is added a solution of 1.76 grams of potassium carbonate in 25 milliliters of water and the heterogeneous mixture stirred vigorously to obtain a 5-oxo-7-trifluoromethylthio-10,11-dihydrobenzo[4,5]-cyclohepta[1,2-b]pyrid-2(1H)one product in the reaction mixture. The latter is recovered washed and dried in the manner previously described.

EXAMPLE VI

In operations carried out in a manner similar to that described in Example I, compounds based on the formula:

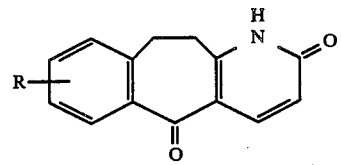

and having different substituents, R, and being either saturated or unsaturated in the cycloheptane ring may be prepared.

TABLE I

| Compound | R | Sat'd/Unsat'd |
|---|---|---|
| VIA | 8-(CH$_3$)$_2$CHO | Unsat'd |
| VIB | 7-I | Sat'd |
| VIC | 7-C$_2$H$_5$O | Sat'd |
| VID | 9-Br | Unsat'd |
| VIE | 7-Br | Unsat'd |

EXAMPLE VII

In operations carried out in a manner similar to that described in Example II, compounds based on the formula:

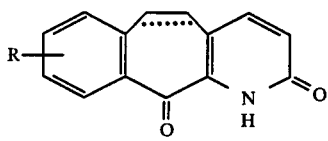

and having different substituents for R and being either saturated or unsaturated in the cycloheptane ring may be prepared:

TABLE II

| Compound | R | Sat'd/Unsat'd |
|---|---|---|
| VIIA | 7-nC$_4$H$_9$O | Unsat'd |
| VIIB | 8-CH$_3$S | Unsat'd |
| VIIC | 9-(CH$_3$)$_3$CO | Sat'd |
| VIID | 9-Br | Unsat'd |
| VIIE | 7-Cl | Sat'd |

EXAMPLE VIII

5-Hydroxy-benzo[4,5]cyclohepta[1,2-b]pyrid-2(1H)one

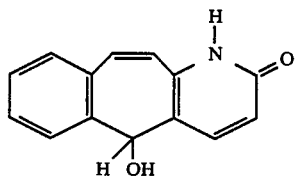

A solution of 0.30 gram (8 millimoles) of sodium borohydride in 5 milliliters of water is added to a solution of 0.70 gram (3 millimoles) of 5-oxo-benzo[4,5]cyclohepta[1,2-b]pyrid-2(1H)one (prepared as described in Example I) in 50 milliliters of methanol and the resulting mixture heated for about twenty minutes at reflux temperature to obtain the desired 5-hydroxy-benzo[4,5]cyclohepta[1,2-b]pyrid-2(1H)one in the reaction mixture. The product is recovered by evaporating the solvent, and washing and drying the residue.

EXAMPLE IX

In operations similar to that described in Example VIII, the following compounds are prepared from the corresponding keto compound of Examples II–VII by reduction with sodium borohydride:
11-Hydroxy-benzo[5,6]cyclohepta[1,2-b]pyrid-2(1H)one.
9-Bromo-11-hydroxy-benzo[5,6]cyclohepta[1,2-b]pyrid-2(1H)one.
9-Cyano-11-hydroxy-5,6-dihydrobenzo[5,6]cyclohepta[1,2-b]pyrid-2(1H)one.
5-Hydroxy-7-trifluoromethylthio-10,11-dihydrobenzo[4,5]cyclohepta[1,2-b]pyrid-2(1H)one.
5-Hydroxy-8-isopropoxybenzo[4,5]cyclohepta[1,2-b]pyrid-2(1H)one.
5-Hydroxy-7-iodo-10,11-dihydrobenzo[4,5]cyclohepta[1,2-b]pyrid-2(1H)one.
7-Ethoxy-5-hydroxy-10,11-dihydrobenzo[4,5]cyclohepta[1,2-b]pyrid-2(1H)one.
9-Bromo-5-hydroxybenzo[4,5]cyclohepta[1,2-b]pyrid-2(1H)one.
7-Bromo-5-hydroxybenzo[4,5]cyclohepta[1,2-b]pyrid-2(1H)one.
7-(n-Butoxy)-11-hydroxybenzo[5,6]cyclohepta[1,2-b]pyrid-2(1H)one.
11-Hydroxy-8-methylthiobenzo[5,6]cyclohepta[1,2-b]pyrid-2(1H)one.
9-(t-Butoxy)-11-hydroxy-5,6-dihydrobenzo[5,6]cyclohepta[1,2-b]pyrid-2(1H)one.
9-Bromo-11-hydroxybenzo[5,6]-cyclohepta[1,2-b]pyrid-2(1H)one.
7-Chloro-11-hydroxy-5,6-dihydrobenzo[5,6]cyclohepta[1,2-b]pyrid-2(1H)one.

EXAMPLE X 5000 compressed tablets, each containing as active ingredient 10 milligrams of the crystalline 5-oxo-benzo[4,5]cyclohepta[1,2-b]pyrid-2(1H)one 0.25 methanol solvate are prepared from the following formulation:

|  | Grams |
|---|---|
| Active ingredient | 50 |
| Starch | 70 |
| Dibasic calcium phosphate hydrous | 500 |
| Calcium stearate | 2.5 |

The ingredients are finely powdered, mixed well, and then granulated with 10 percent starch paste. The granulation is dried and compressed into tablets using starch as a disintegrant and calcium stearate as lubricant.

EXAMPLE XI 10,000 hard gelatin capsules, each containing 25 milligrams of 11-oxo-benzo[5,6]cyclohepta[1,2-b]pyrid-2(1H)one are prepared from the following formulation:

|  | Grams |
|---|---|
| Active ingredient | 250 |
| Lactose | 750 |
| Starch | 250 |
| Talc | 250 |
| Calcium stearate | 10 |

A uniform mixture of the active and supplementary ingredients is prepared and filled into two-piece hard gelatin capsules. The capsules are suitable for oral administration to provide therapeutic relief for patients with cardiovascular diseases.

Preparation of the Starting Materials

The starting oxobenzopyridine (or azaketone) compounds which may be represented by the formula:

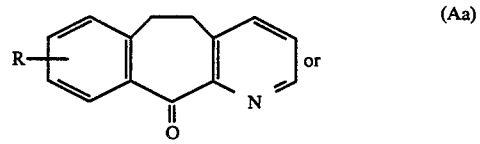
(Aa)

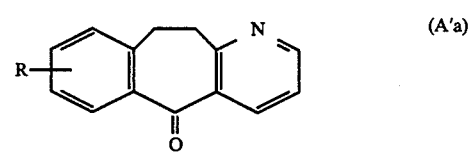
(A'a)

may be prepared by the cyclization of the appropriately substituted β-phenylethylpyridine carboxylic acid or nitrile using a large excess of polyphosphoric acid.

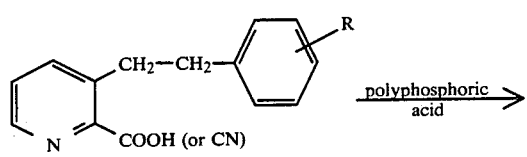

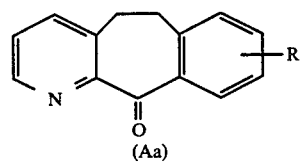

(Aa)

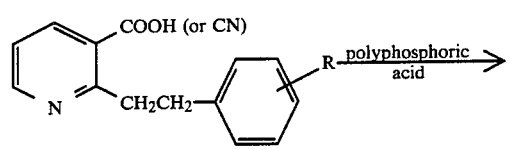

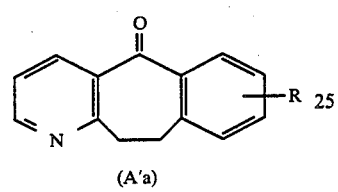

(A'a)

For carrying out the cyclization, the appropriate phenethylpyridine nitrile or acid is heated with about fifty times its weight of polyphosphoric acid at 140°–160° C. for about six hours. The hot solution is poured onto ice, made basic with sodium hydroxide and then extracted with either or chloroform. The extracts are dried and the solvent evaporated from the dried solution to obtain the azaketone compounds as residue. The azaketone compounds may be purified by crystallization or chromatography.

The starting oxypyridine or azaketone compounds which may be represented by the formula:

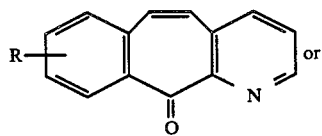

(Ab)

or

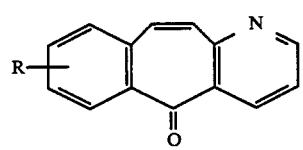

(A'b)

may be prepared by the selenium dioxide oxidation of the compounds of Formula Aa or A'a.

For carrying out the oxidation, the compound of Formula Aa or A'a, selenium dioxide and pyridine are heated together at reflux temperature for about 3 to 18 hours. At the end of this period, the reaction mixture is allowed to cool and is then filtered. The filtrate is subjected to reduce pressure to remove the solvent pyridine and to recover the crude product as residue. It may be purified by dissolving in dilute hydrochloric acid, basifying the solution with ammonia to obtain crystals of compound of Formula Ab or A'b. The crystals may be further purified by recrystallization.

The β-phenylethylpyridinecarboxylic acid:

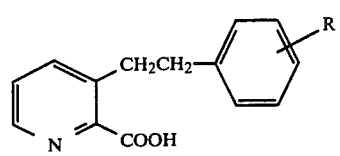

used to produce the compound of Formula Aa may be prepared through the following sequence of reactions:

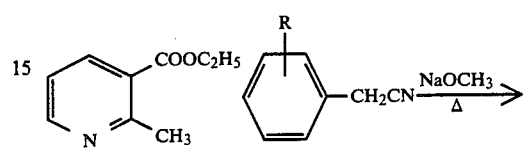

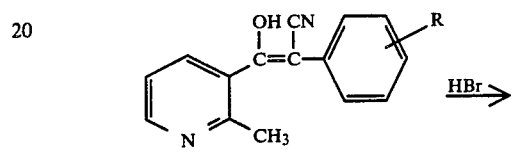

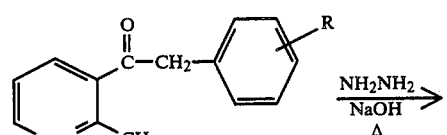

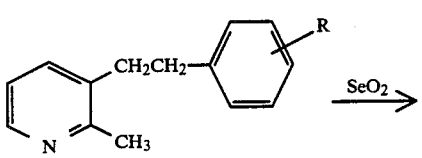

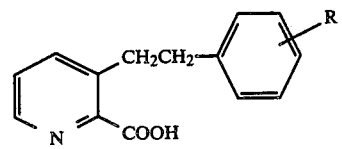

In carrying out the reaction, an appropriate ethyl 2-methylnicotinate and an appropriate phenylacetonitrile are added to a stirred refluxing solution of sodium methoxide and the mixture heated on the steam bath for 4 to 6 hours. The reaction is then quenched with ice water, and the α-cyano-β-[2-methyl-3-pyridyl]-β-hydroxystyrene intermediate recovered from the mixture by acidifying the mixture to precipitate the intermediate.

The hydroxystyrene intermediate is then refluxed for about 16 hours with 48 percent hydrobromic acid, and thereafter poured into ice water. The ice water mixture is made basic with ammonia to obtain a benzyl-2-methyl-3-pyridyl ketone. The ketone is recovered by extracting the aqueous solution with chloroform and distilling.

The ketone is reduced by mixing with sodium hdyroxide and hydrazine hydrate in diethylene glycol and heating to 240° C. with continuous removal of water and maintaining the mixture at this temperature for 3 hours to obtain a 2-methyl-3-phenylethylpyridine intermediate. The latter is recovered by cooling the reaction mixture, pouring into water and extracting with ether, and then drying and distilling the ether extracts.

The 2-methyl-3-phenylethylpyridine is converted to 3-phenylethylpicolinic acid by oxidizing 2-methyl-3-phenylethylpyridine with selenium dioxide employing conventional selenium dioxide oxidizing conditions.

The β-phenylethylpyridinecarboxylic acid:

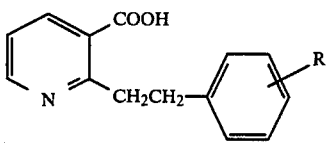

used to produce the compound of Formula A'a may be prepared through the following sequence of reactions:

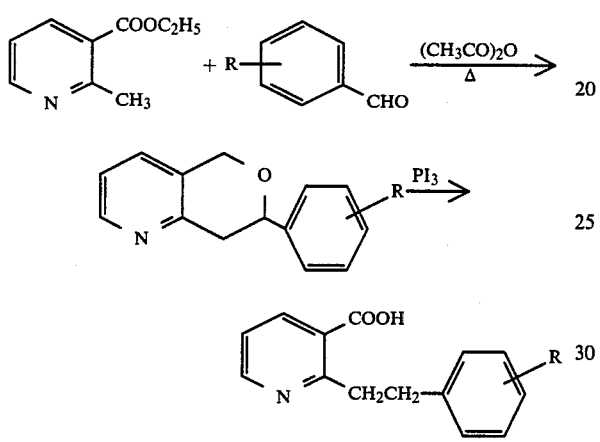

In carrying out the reaction, an appropriate ethyl 2-methylnicotinate and benzaldehyde compound and acetic anhydride are refluxed together under nitrogen for about 24 hours. Thereafter, the excess anhydride is removed in vacuo and the residue poured into water and extracted with ether. The ether solution extracted with dilute acid, the acid solution then made basic with ammonia to obtain a lactone of 2-(2-hydroxy-2-phenylethyl)nicotinic acid. The lactone is reduced to 2-phenylethylnicotinic acid adding the lactone to a freshly prepared mixture of phosphorus and iodine and the resulting mixture heated at reflux temperature for 3 to 10 hours with stirring. The acid is recovered from the reaction mixture by filtering to remove the phosphorus and cooling to recover the hydroiodic acid salt which is collected, dissolved in water and the solution neutralized with ammonia to obtain the 2-phenethylnicotinic acid.

The above procedure as well as alternative methods applicable to the preparation of the starting materials is found in a publication of F. J. Villani et al., J. Het. Chem. 8, 73 (1971).

Certain of the starting materials may be obtained from a bromo or halo-substituted azaketone by heating with an appropriate copper derivative or mercury derivative with copper dust:

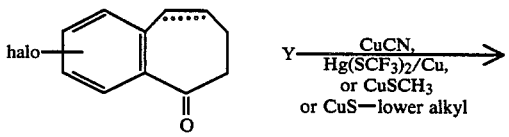

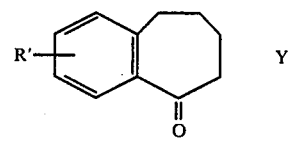

In carrying out the reaction, the appropriate halo-substituted azaketone and metal derivative are heated together at temperatures in the range of about 100°–150° C. in a solvent such as dimethylformamide for several hours with the formation of the cyano, trifluoromethylthio or methylthio substituted azaketone in the reaction mixture. The azaketone may then be recovered from the reaction mixture by pouring into water and water-immiscible organic solvent, stirring vigorously, filtering, separating the phases and recovering the azaketone from the organic phase.

Representative preparations on the use of copper derivatives to introduce substituents in organic structures by replacing the halogen in the appropriate halo-substituted organic compound and employed in or adaptable to the synthesis of the foregoing compounds are described in the publications of D. C. Remy et al., J. Org. Chem. 41, 1644 (1976) and J. Med. Chem. 20, 1013 (1977).

What is claimed is:

1. A compound represented by the formula:

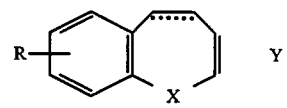

wherein:
the ------- bond designation indicates that the bond may be a saturated single bond or an unsaturated double bond;
X is —C=O or —CHOH;
Y is —NHCOCH=CH—;
wherein the ends of the chain may be attached to the carbon of the ring in either direction so that either —NH— or =CH— is attached to the carbon adjacent to X; and R is hydrogen, lower alkoxy, cyano, halo, trifluoromethylthio or lower alkylthio.

2. A compound according to claim 1 in which the —NH— in —NHCOCH=CH— is attached to the carbon adjacent to X and is represented by the formula:

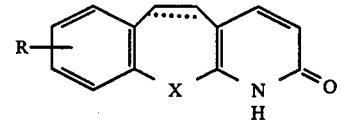

3. A compound according to claim 1 in which the =CH— in —NHCOCH=CH— is attached to the carbon adjacent to X and is represented by the formula:

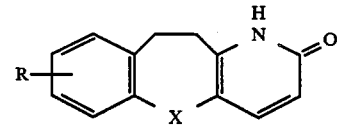

4. A compound according to claim 1 in which X is C=O.

5. A compound according to claim 3 in which X is C=O, R is H and is named 5-oxo-benzo[4,5]cyclohepta[1,2-b]pyrid-2(1H)one.

6. A compound according to claim 2 in which X is C=O, R is H and is named 11-oxo-benzo[5,6]cyclohepta[1,2-b]pyrid-2(1H)one.

7. A compound according to claim 2 in which X is C=O, R is Br and is named 9-bromo-11-oxo-benzo[5,6-]cyclohepta[1,2-b]pyrid-2(1H)one.

8. A pharmaceutical composition useful for treatment of patients suffering from congestive heart failure comprising a cardiotonic amount of a compound having the formula:

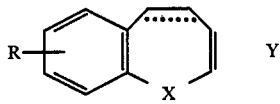

wherein:
the ....... bond designation indicates that the bond may be a saturated single bond or an unsaturated double bond;
X is —C=O or —CHOH;
Y is —NHCOCH=CH=;
wherein the ends of the chain may be attached to the carbon of the ring in either direction so that either —NH— or =CH— is attached to the carbon adjacent to X; and
R is hydrogen, lower alkoxy, cyano, halo, trifluoromethylthio, or lower alkylthio; and a pharmaceutically acceptable carrier.

9. A method for treating congestive heart failure which comprises administering to a patient suffering from congestive heart failure, a therapeutic amount of a compound having the formula:

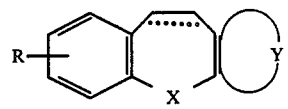

wherein:
the ....... bond designation indicates that the bond may be a saturated single bond or an unsaturated double bond;
X is —C=O or —CHOH;
Y is —NHCOCH=CH—;
wherein the ends of the chain may be attached to the carbon of the ring in either direction so that either —NH— or =CH— is attached to the carbon adjacent to X; and
R is hydrogen, lower alkoxy, cyano, halo, trifluoromethylthio, or lower alkylthio.

* * * * *

UNITED STATES PATENT AND TRADEMARK OFFICE
CERTIFICATE OF CORRECTION

PATENT NO. : 4,639,457
DATED : January 27, 1987
INVENTOR(S) : DAVID C. REMY

Page 1 of 2

It is certified that error appears in the above—identified patent and that said Letters Patent is hereby corrected as shown below:

IN THE SPECIFICATION:

Column 1, lines 11-14, structure should be

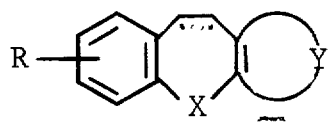

circle missing

IN THE CLAIMS:

Claim 1, column 14, lines 30-35, structure should be

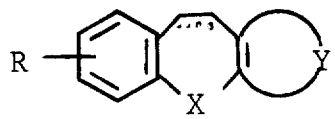

circle missing

UNITED STATES PATENT AND TRADEMARK OFFICE
CERTIFICATE OF CORRECTION

PATENT NO. : 4,639,457

DATED : January 27, 1987

INVENTOR(S) : David C. Remy

It is certified that error appears in the above-identified patent and that said Letters Patent is hereby corrected as shown below:

Claim 8, column 15, lines 16-23, structure should be

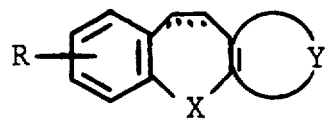

Circle missing

Signed and Sealed this

Eleventh Day of August, 1987

Attest:

DONALD J. QUIGG

Attesting Officer

Commissioner of Patents and Trademarks